United States Patent
Jung

(10) Patent No.: US 8,845,706 B2
(45) Date of Patent: Sep. 30, 2014

(54) MEDICAL TREATMENT APPARATUS FOR EXPOSING TUMOR MASS

(75) Inventor: Bok Won Jung, Seogwipo-si (KR)

(73) Assignee: Bok Won Jung, Seogwipo-Si, Jeju-Do ( * ) Notice: Subject to any disclaimer, the term of this patent is extended or adjusted under 35 U.S.C. 154(b) by 441 days.

(21) Appl. No.: 13/212,603

(22) Filed: Aug. 18, 2011

(65) Prior Publication Data

US 2012/0046717 A1 Feb. 23, 2012

(30) Foreign Application Priority Data

Aug. 20, 2010 (KR) .......................... 10-2010-0080739

(51) Int. Cl.
*A61B 18/14* (2006.01)
*A61F 7/00* (2006.01)
*A61F 7/02* (2006.01)
*A61F 7/03* (2006.01)

(52) U.S. Cl.
CPC ........... *A61F 7/00* (2013.01); *A61F 2007/0217* (2013.01); *A61F 7/032* (2013.01); *A61F 2007/0056* (2013.01)
USPC .............................................. 607/96; 607/27

(58) Field of Classification Search
USPC .......................... 606/27–31; 607/96, 108–114; 431/298–325
See application file for complete search history.

(56) References Cited

U.S. PATENT DOCUMENTS 6,453,202 B1 * 9/2002 Knowlton ...................... 607/102
7,238,183 B2 * 7/2007 Kreindel ......................... 606/41

* cited by examiner

*Primary Examiner* — Michael Peffley
(74) *Attorney, Agent, or Firm* — Lowe Hauptman & Ham, LLP

(57) ABSTRACT

A medical treatment apparatus applies heat to the skin so that the skin may be gradually collapsed without incision and thereby a tumor mass beneath the skin may be exposed to the outside and allowed to be removed. This apparatus includes a cup-like container, oil, and a wick. The container is placed on the first part of the skin that covers a target tumor, and has a vertically penetrated cylindrical shape. The oil is contained in the container and is in contact with the first part of the skin. The wick is placed in the oil so as to catch flame. The temperature of the oil gradually rises while the flame lives on the wick, so heat is continuously applied to the first part of the skin from the oil. This apparatus may further include at least one of a cooling unit and a cooling water pipe placed at an outside of the container, enclosing the container, being in contact with the second part of the skin that is located at the outside of the container, and cooling the second part of the skin. This apparatus may also include an adhesive interposed between the container and the first part of the skin.

13 Claims, 6 Drawing Sheets

MEDICAL TREATMENT APPARATUS FOR EXPOSING TUMOR MASS

BACKGROUND OF THE INVENTION

1. Field of the Invention

The present invention relates in general to a medical treatment apparatus for exposing a tumor mass and, more particularly, to a medical treatment apparatus that applies heat to the skin so that the skin may be gradually collapsed without incision and thereby a tumor mass beneath the skin may be exposed to the outside and allowed to be removed.

2. Description of the Related Art

A tumor is an abnormal growth caused by the uncontrolled division of cells. A tumor may be visible or palpated on the skin or protrude outward from the body.

Benign tumors do not have the potential to spread to other parts of the body (i.e., a process called metastasis) and are curable by surgical removal. Malignant or cancerous tumors, however, may metastasize to other parts of the body and will ultimately result in death if not successfully treated by surgery and/or other methods.

Surgical removal is one of well known ways of treating tumors. Chemotherapy, radiation therapy, and biological therapy are other treatment options. Because benign tumors do not have the potential to metastasize, they are often treated successfully with surgical removal alone. Malignant tumors, however, are most often treated with a combination of surgery and chemotherapy and/or radiation therapy.

Unfortunately, surgery requires a complex and sophisticated process such as anesthesia, incision of the skin, tumor removal, and closure of the skin. Additionally, other tumor treatment options may often give rise to various side effects such as vomiting, nausea, loss of hair, diarrhea, anorexia, and the like.

BRIEF SUMMARY OF THE INVENTION

Accordingly, the present invention is to address the above-mentioned problems and/or disadvantages and to offer at least the advantages described below.

One aspect of the present invention is to provide a medical treatment apparatus that allows easy and convenient removal of tumors located under the skin without requiring anesthesia and incision.

Another aspect of the present invention is to provide a medical treatment apparatus that can minimize or prevent undesirable side effects caused by tumor removal.

According to one aspect of the present invention, provided is a medical treatment apparatus comprising: a heating unit located on a first part of a skin that covers a tumor, and applying heat to the first part of the skin; and a cooling unit placed at an outside of the heating unit, enclosing the heating unit, being in contact with a second part of the skin that is located at the outside of the heating unit, and cooling the second part of the skin.

In this apparatus, the heating unit may include a cup-like container having a vertically penetrated cylindrical shape, oil contained in the container and being in contact with the first part of the skin, and a wick placed in the oil so as to catch flame, and also the cooling unit may be formed of metallic material.

This apparatus may further comprise a cooling water pipe placed on the cooling unit at the outside of the heating unit and configured to contain cooling water or to allow a flow of the cooling water.

This apparatus may further comprise a cooling water pipe integrated into the cooling unit and configured to contain cooling water or to allow a flow of the cooling water.

In this apparatus, the cooling unit may have a property of being bendable to conform to surface contours of the skin.

According to another aspect of the present invention, provided is a medical treatment apparatus comprising: a cup-like container placed on a first part of a skin that covers a target tumor, and having a vertically penetrated cylindrical shape; oil contained in the container and being in contact with the first part of the skin; and a wick placed in the oil so as to catch flame, wherein a temperature of the oil gradually rises while the flame lives on the wick and thereby heat is continuously applied to the first part of the skin from the oil.

This apparatus may further comprise an adhesive interposed between the container and the first part of the skin.

This apparatus may further comprise a cooling water pipe placed at an outside of the container, enclosing the container, configured to contain cooling water or to allow a flow of the cooling water, being in contact with a second part of the skin that is located at the outside of the container, and cooling the second part of the skin.

This apparatus may further comprise a cooling unit placed at an outside of the container, enclosing the container, being in contact with a second part of the skin that is located at the outside of the container, and cooling the second part of the skin. Additionally, this apparatus may further comprise a cooling water pipe integrated into the cooling unit and configured to contain cooling water or to allow a flow of the cooling water.

In this apparatus, the container may have an inwardly extended lower part.

In this apparatus, the container may have an outwardly extended lower part. Additionally, this apparatus may further comprise a cooling unit placed at an outside of the container, enclosing the container, being in contact with a second part of the skin that is located at the outside of the container, cooling the second part of the skin, and having an inwardly extended upper part that meets the outwardly extended lower part of the container.

The medical treatment apparatus according to aspects of the present invention applies heat to the skin so that the skin may be gradually collapsed and thereby a tumor mass beneath the skin may be exposed to the outside. Therefore, this apparatus allows easy and convenient removal of tumors without incision.

Since allowing a heat-based therapy that exposes a target tumor under the skin to the outside and then removes the exposed tumor, the medical treatment apparatus according to aspects of the present invention does not require a complex and sophisticated process caused in typical surgical removal and also can minimize or prevent undesirable side effects caused in typical tumor removal techniques.

Other aspects, advantages, and salient features of the invention will become apparent to those skilled in the art from the following detailed description, which, taken in conjunction with the annexed drawings, discloses exemplary embodiments of the invention.

DETAILED DESCRIPTION OF THE INVENTION

Exemplary, non-limiting embodiments of the present invention will now be described more fully with reference to the accompanying drawings. This invention may, however, be embodied in many different forms and should not be construed as limited to the exemplary embodiments set forth herein. Rather, the disclosed embodiments are provided so that this disclosure will be thorough and complete, and will fully convey the scope of the invention to those skilled in the art. The principles and features of this invention may be employed in varied and numerous embodiments without departing from the scope of the invention.

Furthermore, well known or widely used techniques, elements, structures, and processes may not be described or illustrated in detail to avoid obscuring the essence of the present invention. Although the drawings represent exemplary embodiments of the invention, the drawings are not necessarily to scale and certain features may be exaggerated or omitted in order to better illustrate and explain the present invention.

Figure 1:
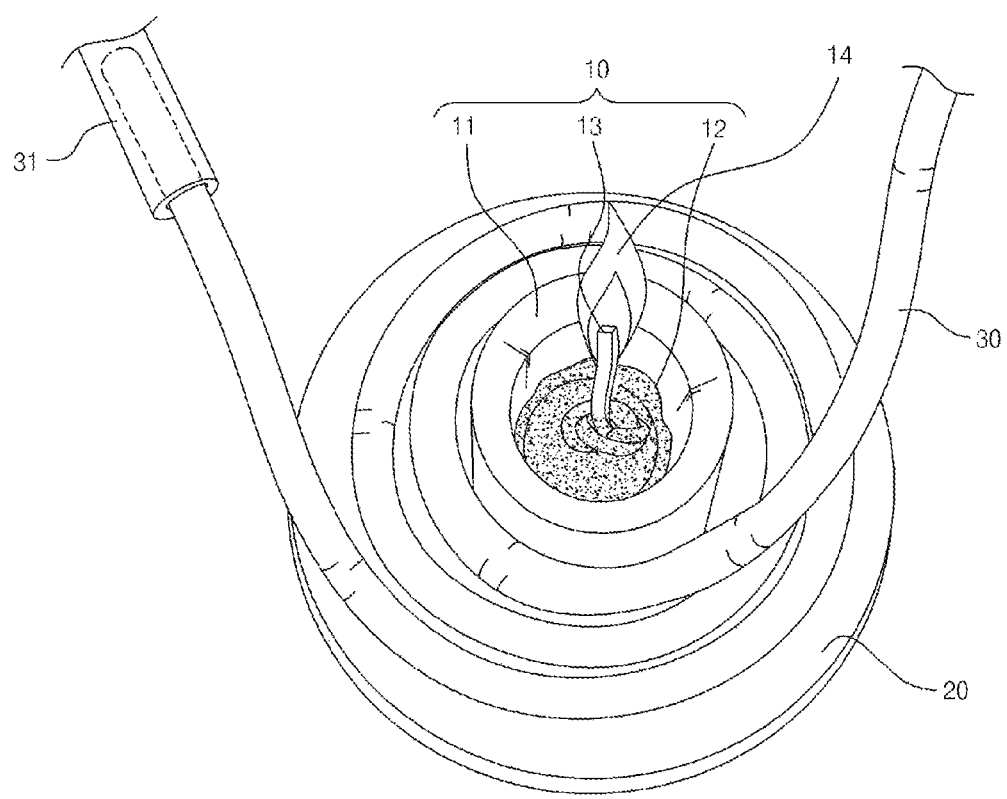
FIG. 1 is a perspective view illustrating a medical treatment apparatus for exposing a tumor in accordance with an exemplary embodiment of the present invention.
Figure 2:
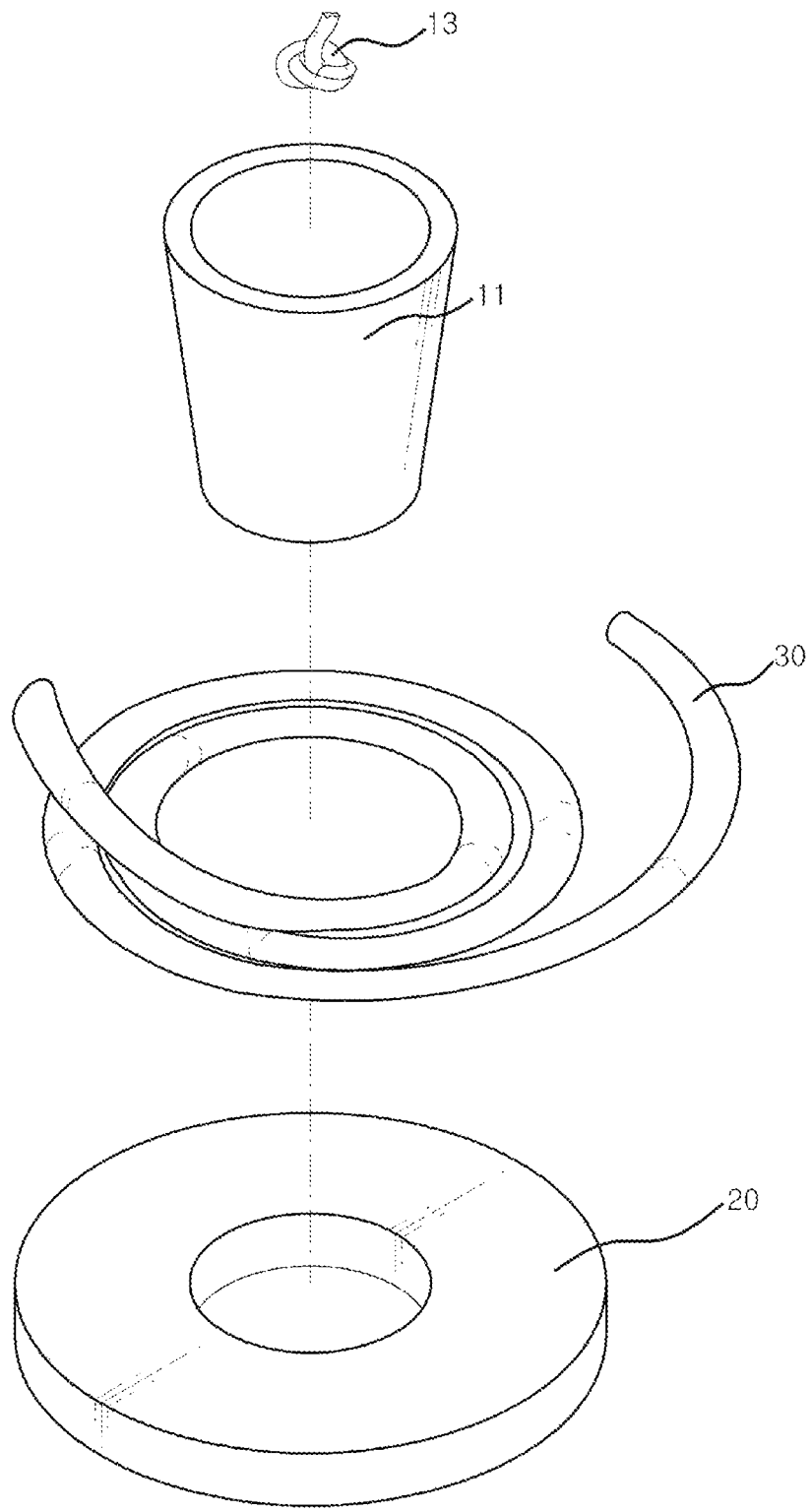
FIG. 2 is an exploded perspective view illustrating the medical treatment apparatus shown in FIG. 1.

FIG. 1 is a perspective view illustrating a medical treatment apparatus for exposing a tumor in accordance with an exemplary embodiment of the present invention. FIG. 2 is an exploded perspective view illustrating the medical treatment apparatus shown in FIG. 1, and FIG. 3 is a cross-sectional view illustrating the medical treatment apparatus shown in FIG. 1.

Figure 3:
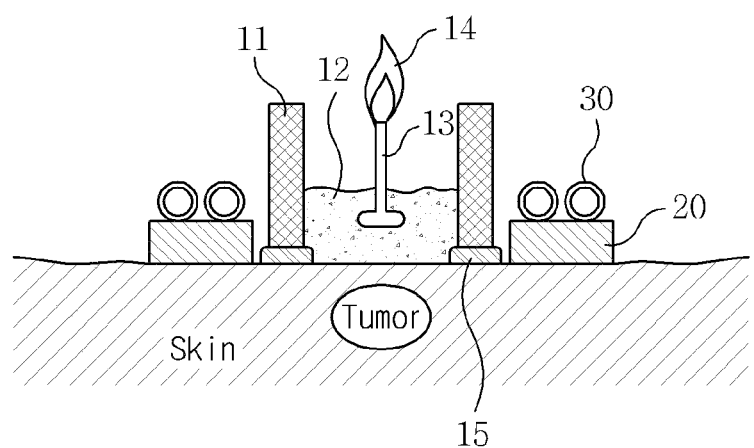
FIG. 3 is a cross-sectional view illustrating the medical treatment apparatus shown in FIG. 1.

Referring to FIGS. 1 to 3, the medical treatment apparatus in this embodiment includes a heating unit 10, a cooling unit 20, and a cooling water pipe 30.

The heating unit 10 is located on the skin under which a tumor exists. The heating unit 10 is used to apply heat to the skin and composed of a cup-like container 11, oil 12, and a wick 13.

The cup-like container 11 has a vertically penetrated cylindrical shape. The cup-like container 11 is placed on the skin that covers a target tumor. Since a tumor is visible or palpated on the skin or protrudes outward from the skin, it is not difficult to determine the position of the cup-like container 11. Preferably, the cup-like container 11 is formed of material with low thermal conductivity. For instance, the cup-like container 11 may be formed of ceramic, plaster, unglazed clay, or the like. Alternatively, the cup-like container 11 may be made by grinding any grain such as starch or rice into flour, mixing the flour and water to make paste, molding the paste into the desired shape, and then drying the molded paste.

The oil 12 is contained in the cup-like container 11 and is in contact with the skin that covers a tumor. For instance, after the cup-like container 11 is put on a target part of the skin, the oil 12 is filled in about one-third of the container 11. The oil 12 may be animal oil or vegetable oil. For instance, animal oil such as cattle oil, horse oil, badger oil, goat oil, dog oil, goose oil, or duck oil may be used, and vegetable oil such as castor oil, olive oil, peanut oil, apricot kernel oil, red pepper seed oil, evening primrose oil, almond oil, camellia oil, coconut palm oil, rape seed oil, sesame oil, perilla oil, grape seed oil, bean oil, or walnut oil.

The wick 13 is a cord or strand placed in the center of the oil 12 so as to catch flame 14. The wick 13 is composed of a twisted circular bottom and an upwardly elongated stem (e.g., 1.5~2 cm in length). When the bottom of the wick 13 sinks in the oil 12, the stem of the wick 13 protrudes from the surface of the oil 12. The wick 13 draws up the oil 12 to flame 14 by capillary action as in a candle or an oil lamp. Preferably, but not limited to, the wick 13 may be formed of traditional Korean paper made from mulberry trees. Alternatively, the wick 13 may be formed of any other suitable material such as fiber.

Meanwhile, as shown in FIG. 3, an adhesive 15 may be interposed between the cup-like container 11 and the skin. For example, the adhesive 15 may use rice starch, wheat flour starch, or the like. The adhesive 15 not only fixes the container 11 on the skin, but also prevents the oil 12 in the container 11 from leaking out. The adhesive 15 may be coated on the skin before the container 11 is placed on the skin. Alternatively, the adhesive 15 may be applied to the lower surface of the container 11, and then the container 11 may be fixed onto the skin. In the former case, the adhesive 15 may be coated on the entire area of the skin to be covered with the container 11 itself and its central penetrated portion. Namely, in this case, the adhesive 15 is also disposed between the oil 12 and the skin.

As discussed above, the heating unit 10 is configured for the cup-like container 11 to hold the oil 12 and for the wick 13 placed in the oil 12 to catch flame 14. The temperature of the oil 12 gradually rises up to about 60~70° C. while the flame 14 lives. Therefore, heat is continuously applied to the skin from the oil 12. With heat acting on the skin, together with softness of the oil 12, skin tissue and muscle are destroyed by degrees, so that the skin is gradually collapsed and leaves space. It is therefore possible to expose a tumor under the skin to the outside without incising the skin by means of a scalpel.

Although the flame 14 lives on the wick 13, the temperature of the oil 12 is merely about 60~70° C. which is favorably bearable for persons. This is similar to the principle of candles. If the temperature of the oil 12 is too high for a person to bear, he or she may put out the flame 14 and make again the flame 14 after a while.

As discussed above, the cup-like container 11 is formed of material with low thermal conductivity. This is for suppressing or preventing a heat transfer toward nearby parts of the skin around a tumor when heat is applied to a target part of the skin on a tumor. In order to enhance this function, the cooling unit 20 and the cooling water pipe 30 are further used for the medical treatment apparatus in this embodiment.

The cooling unit 20 is configured to cool the second part of the skin. In this disclosure, a part of the skin located directly under the heating unit 10 may be referred to as the first part, and other part located at the outside of the heating unit 10 may be referred to as the second part. The cooling unit 20 is placed at the outside of the heating unit 10 and is in contact with the second part of the skin. The cooling unit 20 may have a thin and wide donut shape that encloses the heating unit 10. For an effective removal of heat, the cooling unit 20 may be preferably, but not limited to, formed of metallic material.

It is also desirable that the cooling unit 20 has the maximum area for contact with the skin in order to further improve efficiency of a heat removal. For this, the cooling unit 20 may be formed of copper, aluminum, lead or any other equivalent that has a property of being bendable to conform to surface contours of the skin.

Meanwhile, the cooling water pipe 30 is placed on the cooling unit 20 at the outside of the heating unit 10 and may have a spiral shape that consists of lines wound twice or thrice. In order to further enhance a cooling effect of the cooling unit 20, the cooling water pipe 30 may contain cooling water or allow the flow of cooling water.

The above-discussed medical treatment apparatus for exposing a tumor is exemplary only and not to be considered as a limitation of the present invention. Although the above-discussed apparatus includes both the cooling unit 20 and the cooling water pipe 30, a medical treatment apparatus according to any other embodiment of this invention may include the only one selected between the cooling unit 20 and the cooling water pipe 30. Furthermore, in some cases, a medical treatment apparatus of this invention may be composed of the heating unit 10 alone, including neither the cooling unit 20 nor the cooling water pipe 30. Additionally, a medical treatment apparatus of this invention may be embodied in various forms, which will be exemplarily described hereinafter.

Figure 4:
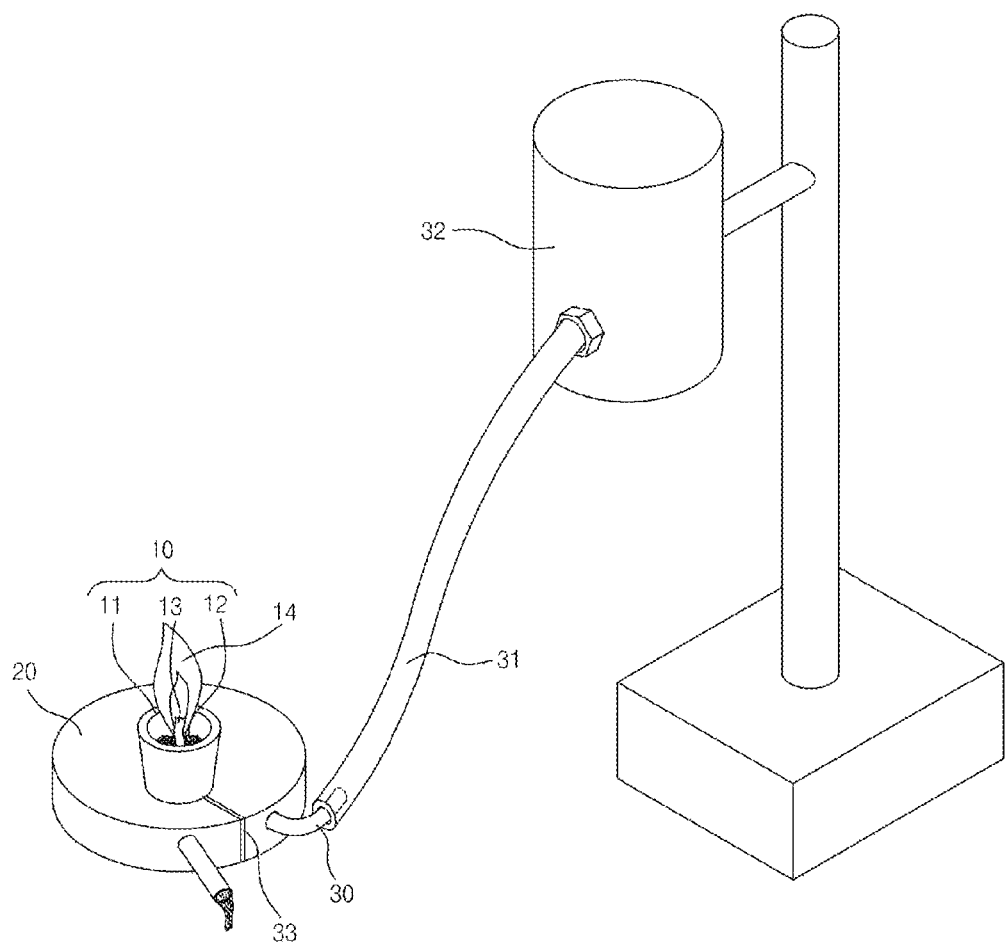
FIG. 4 is a perspective view illustrating a medical treatment apparatus for exposing a tumor in accordance with another exemplary embodiment of the present invention.
Figure 5:
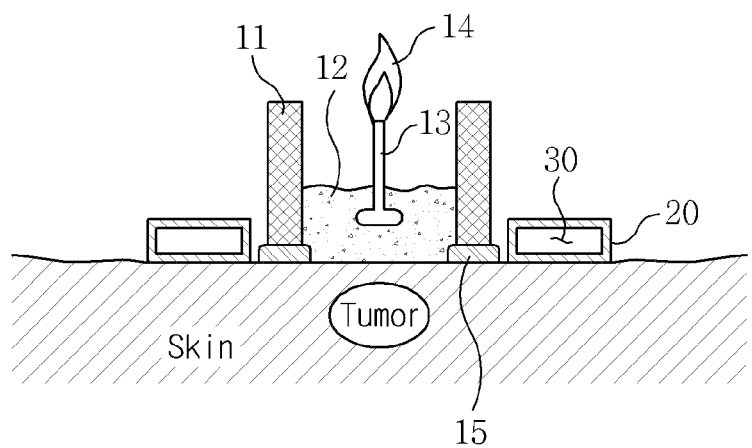
FIG. 5 is a cross-sectional view illustrating the medical treatment apparatus shown in FIG. 4.

FIG. 4 is a perspective view illustrating a medical treatment apparatus for exposing a tumor in accordance with another exemplary embodiment of the present invention. FIG. 5 is a cross-sectional view illustrating the medical treatment apparatus shown in FIG. 4.

Referring to FIGS. 4 and 5, the medical treatment apparatus in this embodiment is composed of the heating unit 10, the cooling unit 20, and the cooling water pipe 30. Particularly, contrary to the previous embodiment in which the cooling water pipe 30 is formed separately from the cooling unit 20, the cooling water pipe 30 in this embodiment is integrated into the cooling unit 20. Therefore, there is no need to separately provide the cooling unit 20 and the cooling water pipe 30. Also, the medical treatment apparatus in this embodiment may have simpler appearance. Meanwhile, the adhesive 15 may be optionally interposed between the container 11 and the skin as shown in FIG. 5.

The cooling water pipe 30 formed in the cooling unit 20 may simply store cooling water or permit the flow of cooling water. In the latter case, the cooling water pipe 30 may have a cooling water inlet and a cooling water outlet both of which communicate with the outside of the cooling unit 20. The cooling water inlet may be connected to a cooling water reservoir tank 32 through a hose 31. Additionally, the cooling water inlet and the cooling water outlet may be closely adjacent to each other and divided by a partition wall 33 formed in the cooling water pipe 30. Therefore, cooling water that flows into the cooling water pipe 30 through the cooling water inlet fails to flow straightly toward the cooling water outlet, runs around the container 11 of the heating unit 10 along the cooling water pipe 30, and drains away through the cooling water outlet. Besides, in some cases, any other necessary typical elements such as a circulation pump for forcing cooling water to circulate may be further used.

Figure 6:
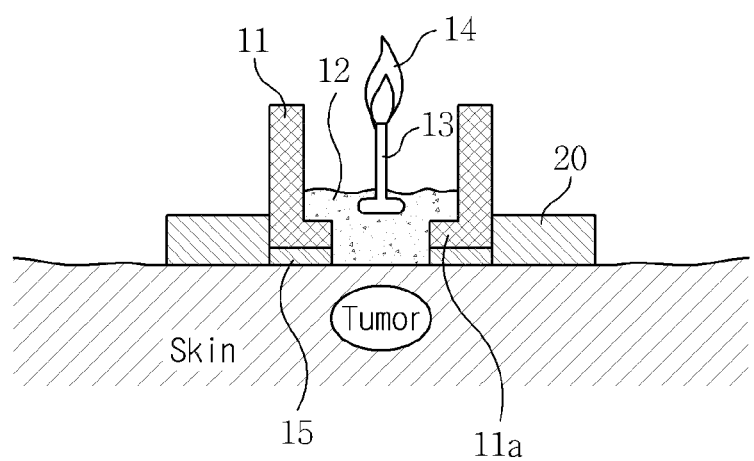
FIG. 6 is a cross-sectional view illustrating a medical treatment apparatus for exposing a tumor in accordance with still another exemplary embodiment of the present invention.

FIG. 6 is a cross-sectional view illustrating a medical treatment apparatus for exposing a tumor in accordance with still another exemplary embodiment of the present invention.

Referring to FIG. 6, the medical treatment apparatus in this embodiment includes the heating unit 10 and the cooling unit 20. Particularly, the cup-like container 11 of the heating unit 10 in this embodiment has an inwardly extended lower part 11a. As in the previous embodiments, the medical treatment apparatus in this embodiment may further include the cooling water pipe located on or in the cooling unit 20. Additionally, in some cases, the medical treatment apparatus in this embodiment may be composed of the heating unit 10 alone without the cooling unit 20, or the cooling water pipe 30 may replace the cooling unit 20.

In this embodiment, the inwardly extended lower part 11a increases a joint area between the adhesive 15 and the container 11. Therefore, the container 11 of the heating unit 10 may be stably fixed to the skin through the adhesive 15.

Figure 7:
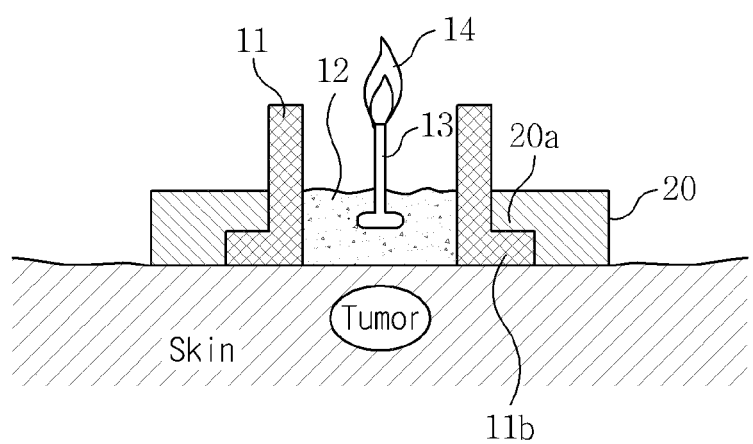
FIG. 7 is a cross-sectional view illustrating a medical treatment apparatus for exposing a tumor in accordance with yet another exemplary embodiment of the present invention.

FIG. 7 is a cross-sectional view illustrating a medical treatment apparatus for exposing a tumor in accordance with yet another exemplary embodiment of the present invention.

Referring to FIG. 7, the medical treatment apparatus in this embodiment includes the heating unit 10 and the cooling unit 20. Particularly, the cup-like container 11 of the heating unit 10 in this embodiment has an outwardly extended lower part 11b, and the cooling unit 20 has an inwardly extended upper part 20a that meets the outwardly extended lower part 11b. As in the previous embodiments, the medical treatment apparatus in this embodiment may further include the cooling water pipe located on or in the cooling unit 20. Additionally, in some cases, the medical treatment apparatus in this embodiment may be composed of the heating unit 10 alone without the cooling unit 20, or the cooling water pipe 30 may replace the cooling unit 20. Although not illustrated, the adhesive may be optionally interposed between the container 11 and the skin as in the previous embodiments.

In this embodiment, the outwardly extended lower part 11b increases a joint area between the adhesive 15 and the container 11 as the inwardly extended lower part 11a shown in FIG. 6 does. Furthermore, the inwardly extended upper part 20a fits nicely the outwardly extended lower part 11b. Therefore, when the cooling unit 20 is disposed around the heating unit 10 placed on the skin, the cooling unit 20 may not allow unstable movements and also be used stably.

While this invention has been particularly shown and described with reference to an exemplary embodiment thereof, it will be understood by those skilled in the art that various changes in form and details may be made therein without departing from the spirit and scope of the invention as defined by the appended claims.

What is claimed is:

1. A medical treatment apparatus comprising:
   a heating unit adapted to be located on a first part of a skin that covers a tumor, and adapted to apply heat to the first part of the skin; and
   a cooling unit configured to be placed at an outside of the heating unit, enclosing the heating unit, adapted to be in contact with a second part of the skin that is located at the outside of the heating unit, and adapted to cool the second part of the skin,
   wherein the heating unit includes a cup-like container having a vertically penetrated cylindrical shape, oil contained in the container and adapted to be in contact with the first part of the skin, and a wick placed in the oil so as to catch flame.

2. The apparatus of claim 1, wherein
   the cooling unit is formed of metallic material.

3. The apparatus of claim 1, further comprising:
   a cooling water pipe configured to be placed on the cooling unit at the outside of the heating unit and configured to contain cooling water or to allow a flow of the cooling water.

4. The apparatus of claim 1, further comprising:
   a cooling water pipe integrated into the cooling unit and configured to contain cooling water or to allow a flow of the cooling water.

5. The apparatus of claim 1, wherein the cooling unit has a property of being bendable.

6. A medical treatment apparatus comprising:
a cup-like container adapted to be placed on a first part of a skin that covers a target tumor, and having a vertically penetrated cylindrical shape;
oil contained in the container and adapted to be in contact with the first part of the skin; and
a wick configured to be placed in the oil so as to catch flame.

7. The apparatus of claim 6, further comprising:
an adhesive configured to be applied to a lower surface of the container.

8. The apparatus of claim 6, further comprising:
a cooling water pipe configured to be placed at an outside of the container, configured to enclose the container, configured to contain cooling water or to allow a flow of the cooling water, adapted to be in contact with a second part of the skin that is located at the outside of the container, and adapted to cool the second part of the skin.

9. The apparatus of claim 7, further comprising:
a cooling unit configured to be placed at an outside of the container, enclosing the container, adapted to be in contact with a second part of the skin that is located at the outside of the container, and adapted to cool the second part of the skin.

10. The apparatus of claim 9, further comprising:
a cooling water pipe integrated into the cooling unit and configured to contain cooling water or to allow a flow of the cooling water.

11. The apparatus of claim 6, wherein the container has an inwardly extended lower part.

12. The apparatus of claim 6, wherein the container has an outwardly extended lower part.

13. The apparatus of claim 12, further comprising:
a cooling unit configured to be placed at an outside of the container, configured to enclose the container, adapted to be in contact with a second part of the skin that is located at the outside of the container, adapted to cool the second part of the skin, and having an inwardly extended upper part that meets the outwardly extended lower part of the container.

* * * * *